US012730165B2

(12) United States Patent
Chu et al.

(10) Patent No.: US 12,730,165 B2
(45) Date of Patent: Sep. 8, 2026

(54) SYSTEM AND METHODS FOR ULTRAFAST WIDEFIELD QUANTUM SENSING USING NEUROMORPHIC VISION SENSORS

(71) Applicant: THE UNIVERSITY OF HONG KONG, Hong Kong (CN)

(72) Inventors: Zhiqin Chu, Hong Kong (CN); Can Li, Hong Kong (CN); Zhiyuan Du, Hong Kong (CN); Gupta Madhav, Hong Kong (CN); Feng Xu, Hong Kong (CN); Ngai Wong, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 148 days.

(21) Appl. No.: 18/698,742

(22) PCT Filed: Nov. 4, 2022

(86) PCT No.: PCT/CN2022/129840
§ 371 (c)(1),
(2) Date: Apr. 4, 2024

(87) PCT Pub. No.: WO2023/078387
PCT Pub. Date: May 11, 2023

(65) Prior Publication Data

US 2024/0426951 A1 Dec. 26, 2024

Related U.S. Application Data

(60) Provisional application No. 63/276,369, filed on Nov. 5, 2021.

(51) Int. Cl.
*G01R 33/32* (2006.01)
*G01N 22/00* (2006.01)
(Continued)

(52) U.S. Cl.
CPC ........... *G01R 33/323* (2013.01); *G01N 22/00* (2013.01); *G01N 33/389* (2024.05); *G01R 33/26* (2013.01); *B82Y 15/00* (2013.01)

(58) Field of Classification Search
CPC ...... G01R 33/032; G01R 33/12; G01R 33/26; G01R 33/32; G01N 22/00; G01V 3/00
See application file for complete search history.

(56) References Cited

U.S. PATENT DOCUMENTS 11,156,674 B2 * 10/2021 Hart ....................... B82Y 20/00
2011/0261354 A1 10/2011 Sinfeld et al.
(Continued)

FOREIGN PATENT DOCUMENTS

WO 2014210486 A1 12/2014

OTHER PUBLICATIONS

Le Sage, et al., "Optical Magnetic Imaging of Living Cells," Nature, Apr. 25, 2013, 496(7446): pp. 486-489.
(Continued)

*Primary Examiner* — Neel D Shah
(74) *Attorney, Agent, or Firm* — Leason Ellis LLP

(57) ABSTRACT

An ultrafast wide-field quantum sensing device using a neuromorphic event-based vision sensor includes a laser generating a laser beam; a dichroic mirror directing the laser beam onto a diamond sample and passing the laser beam reflected from the diamond, and an event camera receiving from the dichroic mirror the beam reflected from the diamond. A source of microwave energy applied to the diamond. A pulse generator synchronizes the microwave source and the event camera to create CW-ODMR measurements, wherein trigger pulses from the pulse generator are applied to the camera and microwave source. The optically detected magnetic resonance (ODMR) resonance frequency is determined based on the CW-ODMR measurements.

6 Claims, 5 Drawing Sheets

(51) Int. Cl.

| | |
|---|---|
| ***G01N 33/00*** | (2006.01) |
| ***G01R 33/26*** | (2006.01) |
| ***G01V 3/00*** | (2006.01) |
| *B82Y 15/00* | (2011.01) |

(56) References Cited

U.S. PATENT DOCUMENTS

| | | | | |
|---|---|---|---|---|
| 2014/0340482 | A1 | 11/2014 | Kanarowski | |
| 2015/0001422 | A1* | 1/2015 | Englund | G01N 21/6486 250/226 |
| 2019/0137398 | A1 | 5/2019 | Entcheva et al. | |
| 2019/0154871 | A1 | 5/2019 | Ledu | |

OTHER PUBLICATIONS

International Search Report and Written Opinion in corresponding International Application No. PCT/CN2022/129840, mailed Jan. 18, 2023.

* cited by examiner

Original
Light intensity(a.u.)
Derivative
Event Sum(a.u.)
Frequency (t)
Sampling
Reconstructing
Positive Event
Negative Event
Frequency (t)
Event Raw Events:
Loop Average:
Spatial Filtering:
Moving Average:
Lorentzian Fitting:

Summed Event Value (a.u.)
300
200
100
0
−100
−200
−300
Forward
Sweeping
2.80 2.81 2.82 2.83 2.84 2.85 2.86 2.87 2.88 2.89 2.90 2.91 2.92 2.93 2.94 2.95
Frequency (GHz)

Summed Event Value (a.u.)
300
200
100
0
−100
−200
−300
Backward
Sweeping
2.80 2.81 2.82 2.83 2.84 2.85 2.86 2.87 2.88 2.89 2.90 2.91 2.92 2.93 2.94 2.95
Frequency (GHz)

Summed Event Value (a.u.)
300
200
100
0
−100
−200
−300
Backwards Sweeping
Forwards Sweeping
2.80 2.81 2.82 2.83 2.84 2.85 2.86 2.87 2.88 2.89 2.90 2.91 2.92 2.93 2.94 2.95
Frequency (GHz)

Light Intensity (a.u.)
0.4
1
Y(μm)
147
0
X(μm) 147
2836
f(MHz)
0.91
1.82
t(s)

Negative Event
Positive Event
Y(μm)
130
0
2836
f(MHz)
35
t(ms)
70
0
X(μm) 173

Light Intensity (a.u.)
1.00
0.98
0.96
0.94
0.92
0.90
Experiment
Fitting
Sensing time: 1.82s
Precision: 0.041MHz
2830 2840 2850 2860 2870 2880 2890 2900 2910
Frequency (MHz)

Event Summation (a.u.)
600
400
200
0
-200
-400
Experiment
Fitting
Sensing time: 1.4s
Precision: 0.046MHz
2830 2840 2850 2860 2870 2880 2890 2900 2910
Frequency (MHz)

SYSTEM AND METHODS FOR ULTRAFAST WIDEFIELD QUANTUM SENSING USING NEUROMORPHIC VISION SENSORS

CROSS-REFERENCE TO RELATED APPLICATION

This application is a U.S. National Phase Application under 35 U.S.C. § 371 of International Patent Application No. PCT/CN2022/129840 filed on Nov. 4, 2022 and claims the benefit of priority to U.S. provisional patent application Ser. No. 63/276,369, filed Nov. 5, 2021, the contents of all of which are hereby incorporated by reference in their entireties. The International Application was published in English on May 11, 2023 as International Publication No. WO/2023/078387 under PCT Article 21 (2).

FIELD OF THE INVENTION

The present invention relates to the measurement of the magnitude and direction of magnetic fields (magnetometry) and, more particularly, to sensitive optical magnetometry based on nitrogen vacancy (NV) centers in diamond, so-called quantum sensing.

BACKGROUND OF THE INVENTION

The sensitive optical magnetometry based on nitrogen vacancy (NV) centers in diamond, so-called quantum sensing, is a promising quantum technology for applications in many aspects ranging from fundamental science to industry. In particular, widefield quantum sensing has been successfully implemented to measure two-dimensional magnetic fields by reading NV fluorescence in parallel using a camera sensor.

However, conventional camera sensors are frame-based. The temporal resolution (i.e., frame per second, FPS) of these sensors is limited (~tens of ms) because of the physical limits of their working mechanism.

In international application WO2014210486 A1 [US Application Publication 2015/0001422] entitled “Wide-field sensing using nitrogen vacancies,” there is disclosed an existing way to achieve widefield quantum sensing with conventional frame-based cameras. According to this application nitrogen-vacancy centers in bulk diamonds and nanodiamonds can be used to sense temperature, pressure, electromagnetic fields, and pH. Unfortunately, conventional sensing techniques use gated detection and confocal imaging, limiting the measurement sensitivity and precluding wide-field imaging. Conversely, the sensing techniques disclosed in this prior application rely on addressing the spins of multiple nitrogen vacancies (NV s) in parallel across a wide field of view and do not require gated detection or confocal imaging. Therefore, it can be used to image temperature, pressure, electromagnetic fields, and pH over wide fields of view. In some cases, wide-field imaging supports spatial localization of the NVs to precisions at or below the diffraction limit. Moreover, the measurement range can extend over extremely wide dynamic range at very high sensitivity.

SUMMARY OF THE INVENTION

The present invention is an ultrafast wide-field quantum sensing device using a neuromorphic event-based vision sensor to achieve a much higher temporal resolution (4 orders of magnitude improvement) than the prior art camera sensors. The temporal resolution (~1 μs) is believed to achieve the world’s best in terms of temporal resolution for widefield quantum sensing.

According to the present invention, event-based cameras, as opposed to frame-based cameras, are used as the sensor for detecting NV fluorescence. Further, the present invention processes the changes in NV fluorescence from the event-based camera in parallel, facilitating ultrafast widefield quantum sensing. Thus, the invention potentially pushes the temporal resolution of widefield quantum sensing by orders of magnitude in principle. The temporal resolution is improved due to the low-level processing capability of the neuromorphic vision sensors, which capture the local changes (events) of NV fluorescence, thereby significantly reducing the required data transmission and thus increasing the temporal resolution. In addition, the neuromorphic vision sensor captures information with a much larger dynamic range and less motion blur, enabling a new avenue for ultrafast widefield magnetometry at the nanoscale that enables investigations of magnetic phenomenon that were too fast to study with the prior art.

BRIEF DESCRIPTION OF THE DRAWINGS

The foregoing and other objects and advantages of the present invention will become more apparent when considered in connection with the following detailed description and appended drawings in which like designations denote like elements in the various views, and wherein:

FIG. 4A shows Forward Sweep, FIG. 4B shows Backward Sweep and FIG. 4C shows the Resonance Frequency $f_{avg}$ calculated, by performing Lorentzian Data-Fitting for measurements in FIG. 4A and FIG. 4B, and then taking an average; FIG. 5A and FIG. 5C show raw frames and Lorentzian spectrum for traditional quantum sensing while FIG. 5B and FIG. 5D show raw events and reconstructed derivate Lorentzian spectrum based on the proposed method.

DETAILED DESCRIPTION OF THE INVENTION

Figure 1A:
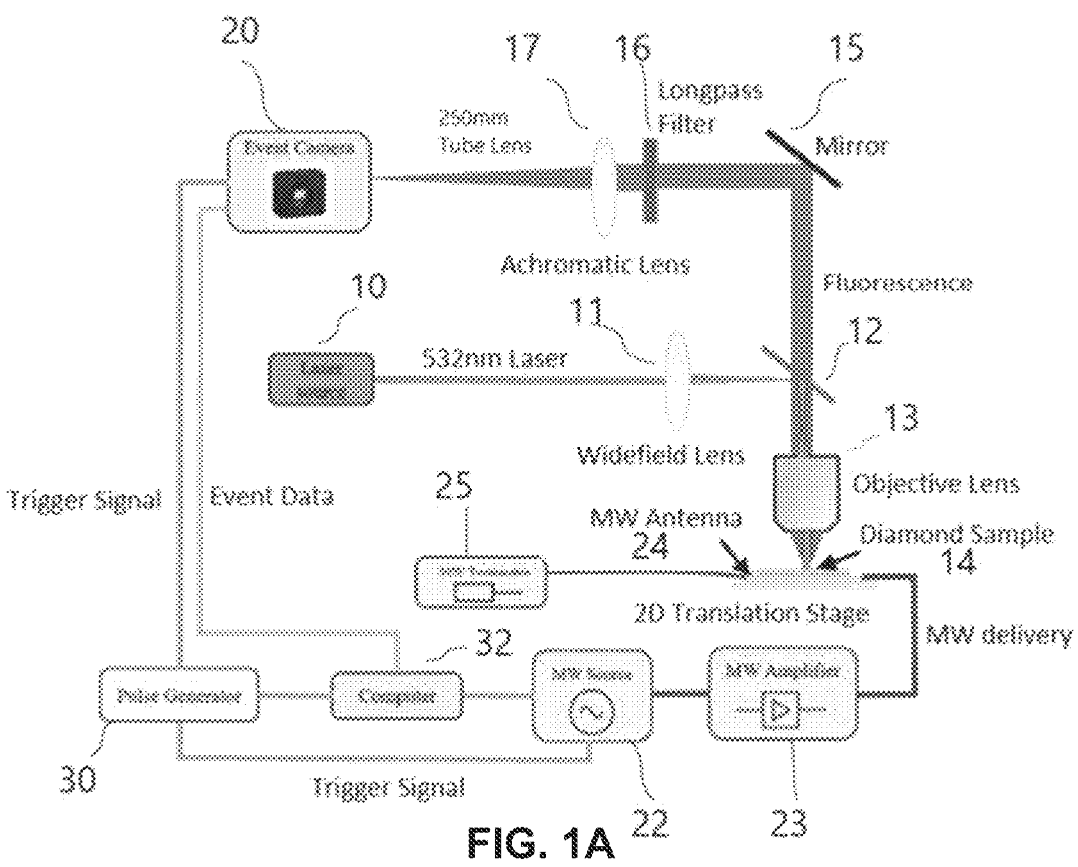
FIG. 1A is a block diagram of an event-based camera widefield quantum sensor microscope of the present invention and FIG. 1B is a photograph of the experimental setup of the event-based camera in a laboratory.

FIG. 1A is a schematic of the setup according to the present invention. A 532 nm laser 10 has its output beam pass through a wide field lens 11 and reflect from a Dichroic Mirror (DM) 12. The reflected beam is focused by an Objective Lens 13 onto a diamond sample 14. The emitted fluorescence from the diamond sample is transmitted back through the DM 12 and is subsequently reflected from a mirror 15 so as to pass through a Long-pass Filter 16 and an Achromatic Lens 17 so it can be detected by the Event Camera 20. An external microwave MW signal from MW source 22 is applied through a MW Amplifier 23 to the diamond sample in order to facilitate the CW-ODMR measurements. As used herein the term “MW source” includes a single microwave generator or a combination of a microwave generator and an arbitrary waveform generator. A MW Antenna 24 with a MW terminator 25 is also attached to the diamond sample.

Figure 1B:
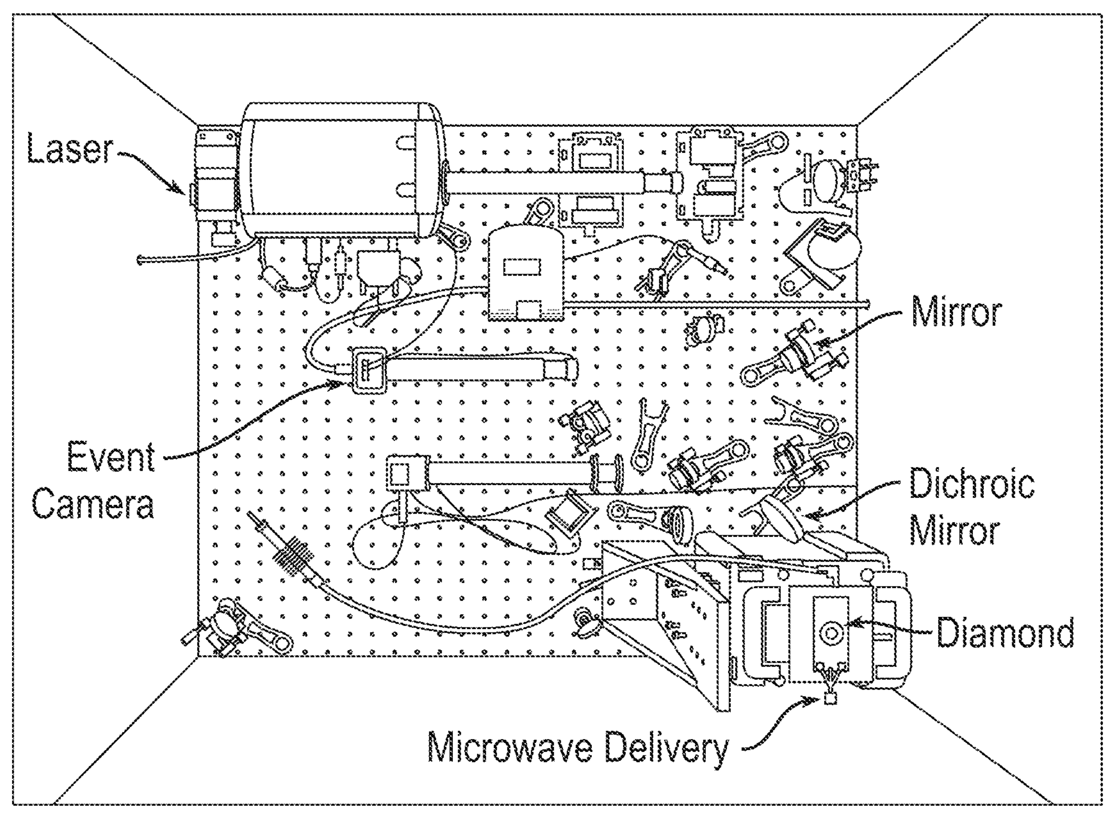

A Pulse Generator 30 is used to synchronize the operations of the Microwave Source 22 and the Event Camera 20. In particular, the signal from the pulse generator 30 is applied to the Event Camera 20 and the MW Source 22 to trigger their operations A computer 32 is used to pre-set working conditions of MW source 22, Event Camera 20 and Pulse Generator 30. The computer 32 also post-processes data sent from Event Camera 20. FIG. 1B is a photograph of the setup.

Figures 2A, 2B:
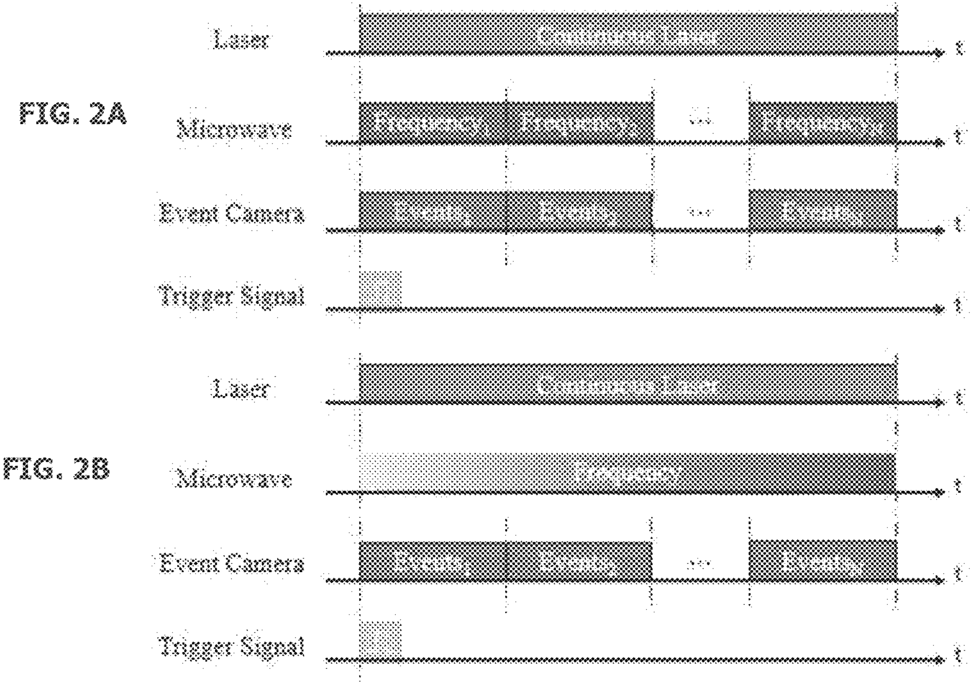
FIGS. 2A and 2B illustrate the protocol for performing the quantum sensing process of the present invention, i.e. CW-ODMR measurements, with step and continuous microwave frequency, respectively.

As shown in FIG. 2A, a Continuous Wave-Optically Detected Magnetic Resonance (CW-ODMR) measurement is performed in a continuous wave CW mode. In the CW mode, the laser, microwave signal, and camera acquisition take place simultaneously. They are synchronized by the external trigger signal from the Pulse Generator 30. The event camera 20 stores the raw event data when the fluorescence change reaches a threshold, which encodes an intensity change as +1 for intensity increasing (positive events) and −1 for intensity decreasing (negative events). In this procedure the microwave frequency is tuned in a stepped way. The sweeping speed can be further accelerated when an Arbitrary Waveform Generator (AWG) is used to continuously tune the frequency as shown in FIG. 2B. Considering the temporal resolution of the event camera to be 1 μs, the total sweeping time can be sub-millisecond.

Figures 3A, 3B:
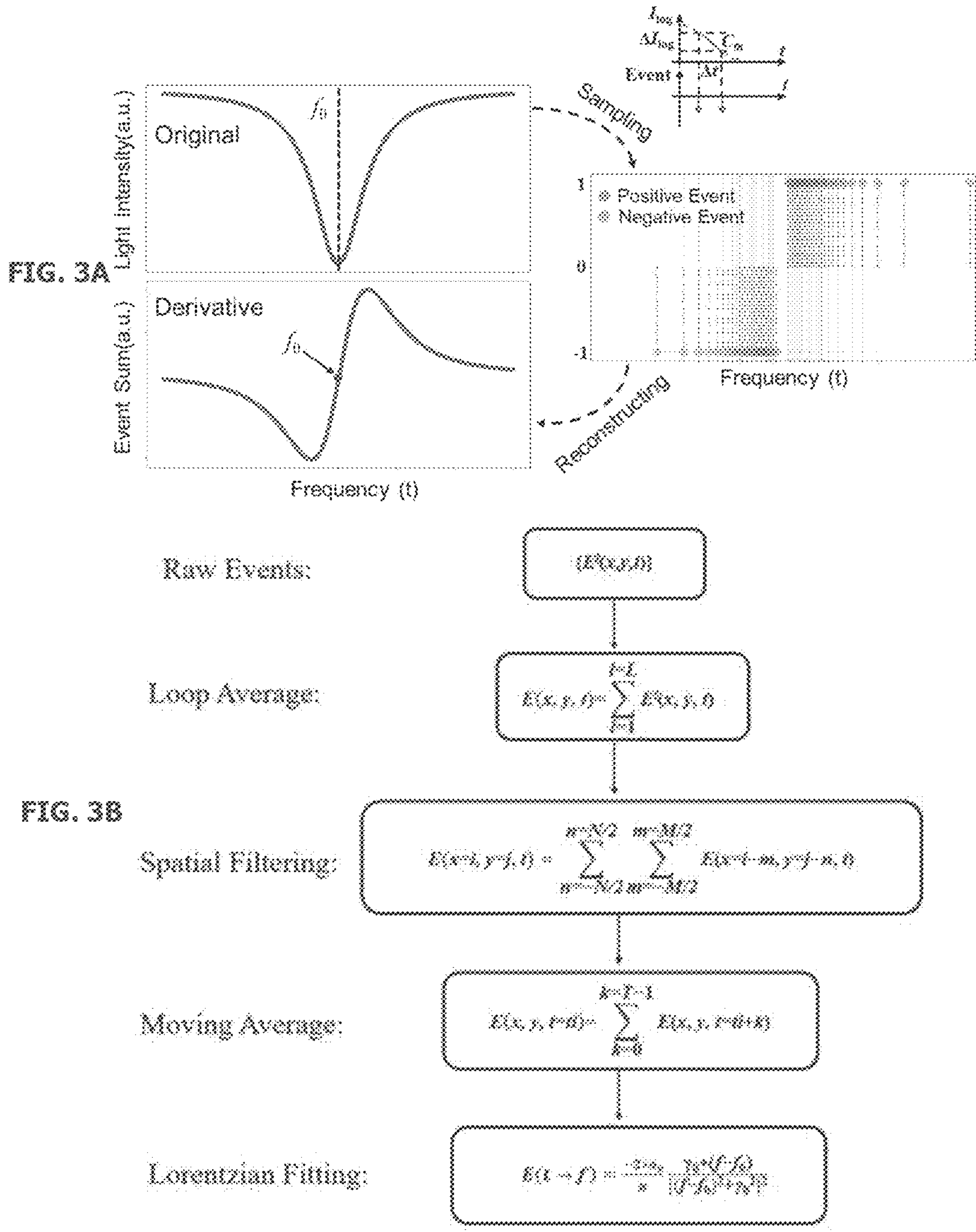
FIG. 3A illustrates the basic principles of the present invention and FIG. 3B is an exemplary flow chart of the steps that can be utilized in processing the raw event data to compute the ODMR resonance frequency.

FIG. 3A illustrates the basic principles of the present invention where light intensity change is detected and compared with a predefined threshold $C_{th}$ after which the original fluorescence spectrum is converted to a series of events. The derivative ODMR spectrum then can be reconstructed by a variety of filtering methods. The flow chart of FIG. 3B shows an example of one of these methods. After sweeping repeatedly for L times, the events of different loops are first summed. Then spatial filtering is carried out by summing up the results of a binning of nearby M*N pixels. These two steps help to reduce noise. After that, the temporal event sequences from a pixel (i.e., a spatial location) are averaged within a time window of T. For a typical fluorescence dip of an NV center, the sensor will produce mainly negative events as frequency tuning moves towards the resonance frequency and mostly positive events when the frequency moves away from the resonance frequency. Therefore, a derivative-like curve of Lorentzian line-type can be reconstructed by summing event values together within a time-window and moving the window across the full sweeping range. In the final step the moving average results are fitted with the derivative of the Lorentzian equation, from which the resonance frequency $f_0$ and linewidth $2\gamma_0$ are determined.

Figures 4A, 4B, 4C:
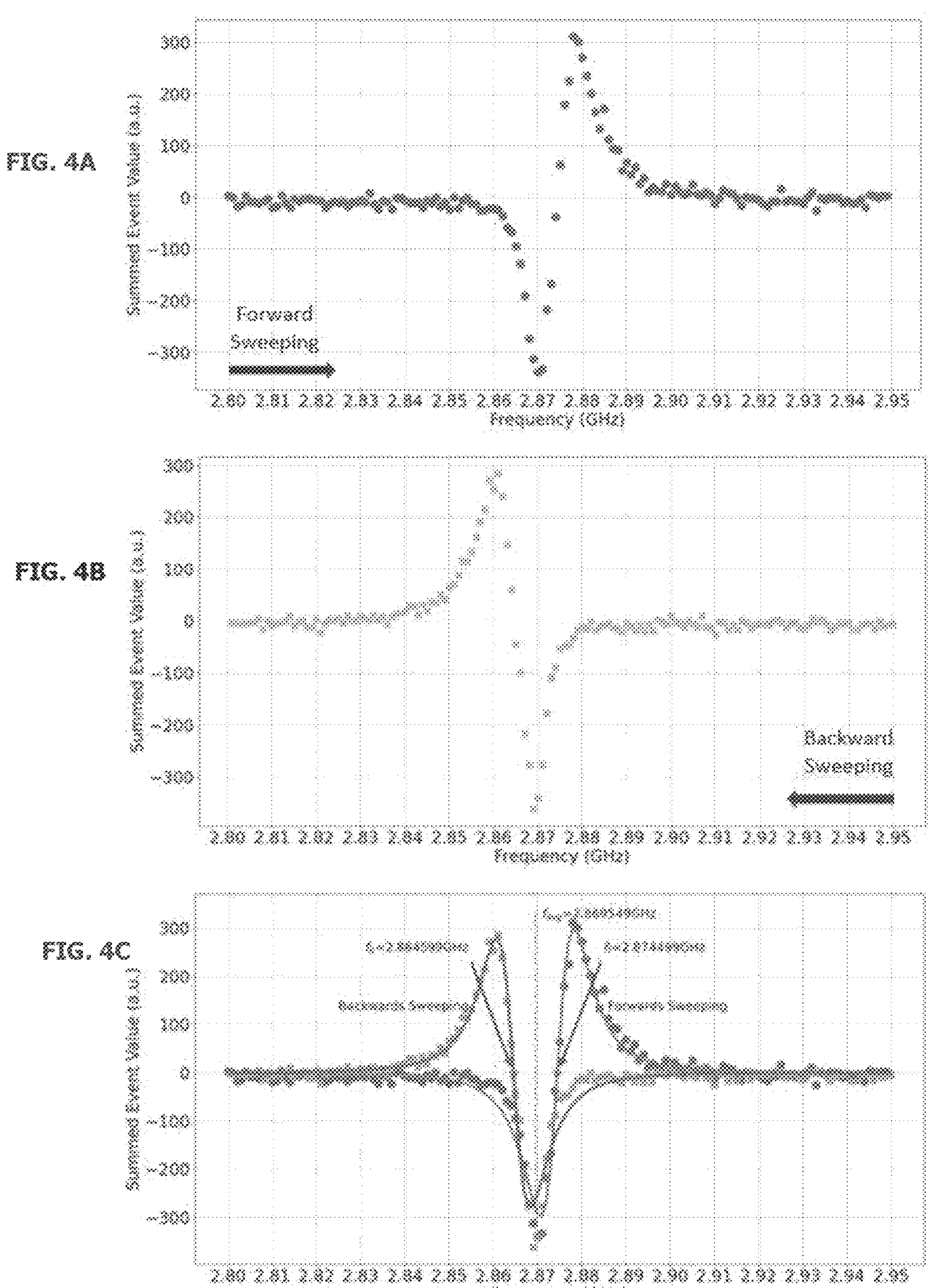
FIGS. 4A-4C are graphs of the summed event value calculated from the post-processing plotted as a function of Microwave Frequency, where

FIGS. 4A-4C are graphs illustrating typical results taken from the central area of the laser spot. These graphs are of the summed event value calculated from the post-processing as a function of microwave frequency. FIG. 4A represents a forward sweep of frequency, FIG. 4B represents a backward sweep and FIG. 4C represents the Resonance Frequency $f_{avg}$ calculated by performing Lorentzian Data-Fitting for measurements in FIGS. 4A and 4B, and then taking an average. After forward and backward sweeping, the two spectra show symmetric deviation from the real resonance frequency. This deviation is then corrected by averaging fitted $f_f$ and $f_b$. The average result $f_{avg}$ equals 2.86955 GHz, which is close to the value of 2.86949 GHz achieved using the prior art EMCCD method. This demonstrates the effectiveness of the present invention.

Figures 5A, 5B, 5C, 5D:
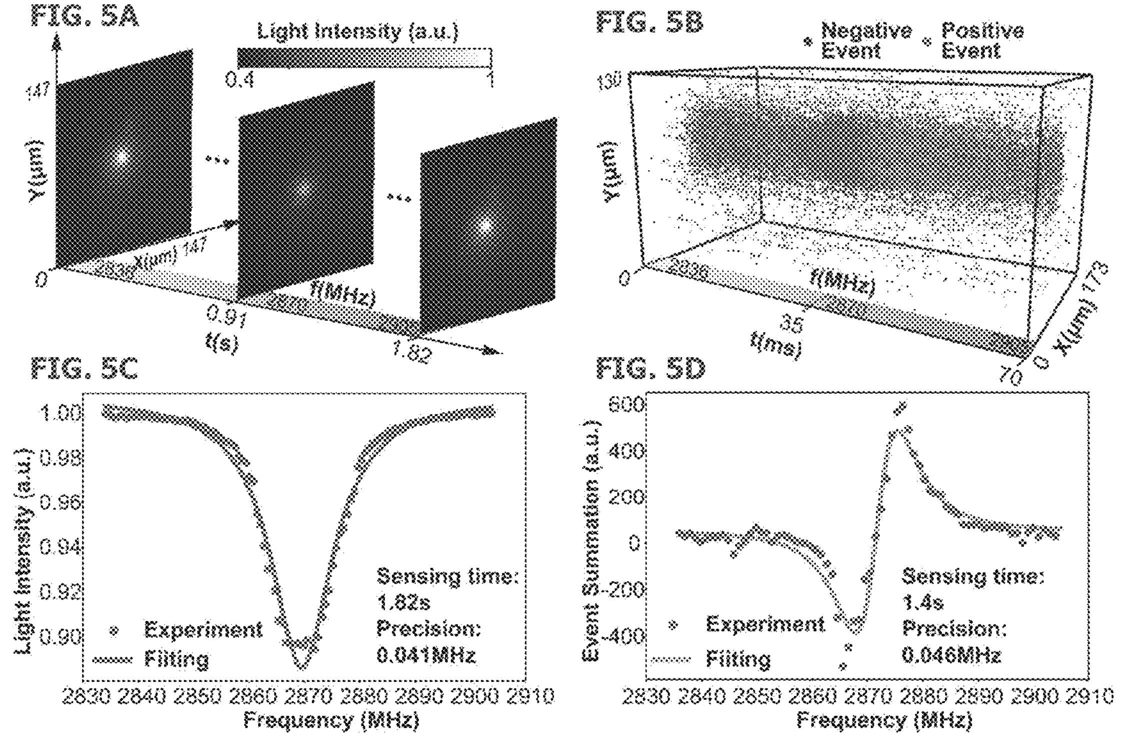
FIGS. 5A-5D are graphs comparing the raw datasets and reconstructed spectrums based on traditional ODMR and the proposed method of the present invention, respectively, where

FIGS. 5A-5D compare the raw datasets and reconstructed spectrums obtained with traditional ODMR and the proposed method of the present invention, respectively. FIG. 5A show raw frames captured with EMCCD and FIG. 5C is the Lorentzian spectrum (discrete and fitted results) taken from the central area of these frames. By contrast, a stream of event points produced by event camera 20 is shown in FIG. 5B. It explicitly illustrates the differences of this invention from traditional method where events are produced with high temporal resolution, while the negative/positive events only assemble near the resonance frequency, i.e. the frequency range when the fluorescence intensity changes most intensely. Correspondingly, the derivative Lorentzian spectrum reconstructed based on the procedures of the present invention mentioned above is illustrated in FIG. 5D. The precision and total measurement time used to extract the resonance frequency are 0.043 MHz/1.82 s for the traditional EMCCD method and 0.046 MHz/1.4 s for the proposed method of the present invention, respectively. Thus, the present invention achieves comparable sensing precision while consumes less time. It should be noted that the sensing speed of the present invention could be further improved by sweeping the frequency faster, while for traditional ODMR it is difficult to do so due to the fixed frame rate of EMCCD.

While the invention is explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. An ultrafast wide-field quantum sensing device using a neuromorphic event-based vision sensor comprising:

- a laser generating a laser beam;
- a dichroic mirror directing the laser beam onto a diamond sample and passing the fluorescence collected from the diamond;
- an event camera receiving from the dichroic mirror the fluorescence reflected from the diamond;
- a long-pass filter and an achromatic lens, wherein the fluorescence from the dichroic mirror to the event camera passes through the long-pass filter and achromatic lens in sequence;
- a source of microwave energy (MW) applied to the diamond;
- a pulse generator for syncing the microwave source and the event camera to create Continuous Wave-Optically Detected Magnetic Resonance (CW-ODMR) measurements, wherein trigger pulses from the pulse generator are applied to the camera and MW source; and
- a computer to control the parameters of the pulse generator and the microwave source wherein the computer also processes raw data transmitted from the event camera.

2. The ultrafast wide-field quantum sensing device of claim 1 wherein the laser is a 532 nm laser.

3. The ultrafast wide-field quantum sensing device of claim 1 further including a microwave antenna with a terminator connected to the diamond.

4. The ultrafast wide-field quantum sensing device of claim 1 further including an objective lens for focusing the laser beam on the diamond.

5. The ultrafast wide-field quantum sensing device of claim 1 wherein the achromatic lens is a 250 mm tube lens.

6. A method of computing the optically detected magnetic resonance (ODMR) resonance frequency, comprising the steps of:

collecting the raw events data from the ultrafast wide-field quantum sensing device of claim 1 for a frequency sweep;

repeating the frequency sweeping for L times;

summing the events of different repeats of the sweeping;

spatial filtering by summing up the results of a binning of nearby M*N pixels; and averaging the temporal event sequences from each pixel with a time window of T.

* * * * *